United States Patent
Lepor

Patent Number: 5,772,631
Date of Patent: Jun. 30, 1998

[54] PROCEDURE FOR ALLEVIATING ARTERIAL OBSTRUCTION

[76] Inventor: Norman E. Lepor, 9770 Apricot La., Beverly Hills, Calif. 90210

[21] Appl. No.: 430,219

[22] Filed: Apr. 28, 1995

[51] Int. Cl.⁶ .................................................. A61M 29/00
[52] U.S. Cl. ............................... 604/96; 600/18; 606/194
[58] Field of Search ................................ 604/22, 96, 101; 600/16–18; 606/192, 194, 195

[56] References Cited

U.S. PATENT DOCUMENTS

| | | |
|---|---|---|
| 4,531,936 | 7/1985 | Gordon . |
| 4,569,332 | 2/1986 | Schiff et al. ........................... 600/18 X |
| 4,697,574 | 10/1987 | Karcher et al. ....................... 600/18 X |
| 4,733,652 | 3/1988 | Kantrowitz et al. .................. 600/18 X |
| 4,741,328 | 5/1988 | Gabbay . |
| 4,911,163 | 3/1990 | Fina .................................... 606/192 X |
| 4,990,139 | 2/1991 | Jang .................................... 606/192 X |
| 5,158,540 | 10/1992 | Wijay et al. . |
| 5,176,619 | 1/1993 | Segalowitz ................................. 600/18 |
| 5,180,367 | 1/1993 | Kontos et al. ....................... 604/194 X |
| 5,195,942 | 3/1993 | Weil et al. ........................... 604/194 X |
| 5,226,889 | 7/1993 | Sheiban ............................... 606/194 X |
| 5,308,319 | 5/1994 | Ide et al. . |
| 5,334,142 | 8/1994 | Paradis . |
| 5,342,297 | 8/1994 | Jang . |
| 5,409,444 | 4/1995 | Kensey et al. . |
| 5,449,342 | 9/1995 | Hirose et al. ........................ 600/16 X |

*Primary Examiner*—Mark Bockelman
*Attorney, Agent, or Firm*—Loeb & Loeb LLP; Michael J. Ram

[57] ABSTRACT

A medical device and method for performing percutaneous transluminal coronary angioplasty (PTCA) and intra-aortic balloon (IAB) counterpropulsion, the device including: a guide catheter insertable into a coronary artery, the guide catheter having an outer surface; an IAB mounted on the outer surface of said catheter; and a PTCA catheter insertable into a coronary artery through the guide catheter, the PTCA catheter including an angioplasty balloon.

2 Claims, 1 Drawing Sheet

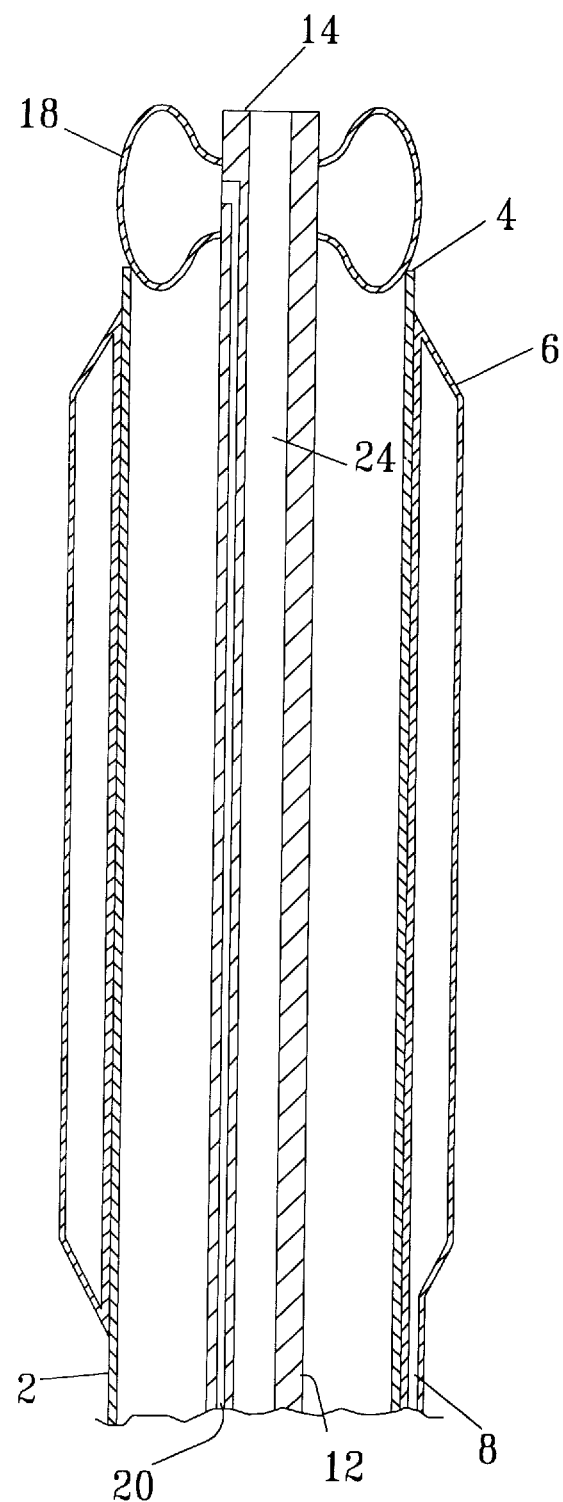

PROCEDURE FOR ALLEVIATING ARTERIAL OBSTRUCTION

BACKGROUND OF THE INVENTION

The present invention relates to medical devices and procedures for alleviating arterial obstructions.

When an obstruction, e.g. a stenosis, occurs in a coronary artery, a common treatment for alleviating the obstruction is known as percutaneous transluminal coronary angioplasty (PTCA). This involves insertion of a balloon into the coronary artery to the location of the obstruction followed by inflation of the balloon to stretch the artery, compress the obstruction and create a clear passage for the flow of blood. After the balloon is deflated and removed, the passage generally remains open, at least for a period of time.

Performance of a PTCA conventionally involves a procedure composed of the following steps, performed in the order described:

- a hollow core needle is introduced through the patient's skin into the femoral artery;
- a first guide wire is inserted into the artery through the needle;
- a vascular sheath, which is essentially a hollow plastic tube, is then inserted through the hollow core needle, over the guide wire;
- after the removal of the guide wire and needle, a hollow plastic coronary guiding catheter with a second guide wire is then introduced through the sheath and, under X-ray guidance, is placed into the coronary artery. The plastic catheter contains a lumen with a diameter sufficient to receive a small PTCA balloon;
- the second guide wire is then removed and a special coronary artery guide wire is inserted under X-ray guidance to the site of the obstruction and then eased past the obstruction towards the end of the artery. A PTCA catheter carrying the PTCA balloon is then placed around the coronary artery guide wire and advanced through the lumen of the guiding catheter to the site of the blockage, while dye is injected into the artery through that lumen to facilitate visualization of the vascular structure to be treated and to assist placement of the balloon in the proper position; and
- the PTCA balloon is then placed at the site of the obstruction and is inflated in order to reestablish a blood flow passage through the artery. Following balloon deflation it is removed with the coronary guide wire.

The success and complication rates of the above procedure vary over a wide range depending, inter alia, on the characteristics of the stenosis and the condition of the patient. Risks associated with the procedure include death, myocardial infarction and the need for emergency bypass surgery. There are occasions when it is difficult to open an artery, or in which the condition of the artery actually worsens and the artery closes during the procedure, resulting in chest pain, shock, or even death. When such a condition, which is evidenced by chest pain, EKG changes and/or hemodynamic instability in the patient, occurs, efforts must be made to stabilize the patient with a minimum delay.

A common technique for dealing with these complications is to place an intra-aortic balloon (IAB) into the aorta, using the other femoral artery from that employed for inserting the PTCA balloon. Placement of an IAB is effected by a technique similar to that described above for inserting a PTCA guide catheter.

An IAB device includes a long catheter extending within the descending aorta and having, on its outer surface, a plastic balloon that can be inflated and deflated in synchronism with the heart rhythm to increase the pressure in the aorta during diastole, and thereby to enhance heart function.

Under the best of circumstances, and even when the operating personnel have sufficient experience, insertion of the IAB takes a certain amount of time, which can be critical in dealing with the emergency condition. Moreover, there will be situations in which the introduction of the IAB will be rendered more difficult by the condition which it is to treat. For example, when a patient develops shock, it sometimes becomes almost impossible to locate the other femoral artery, in which case insertion of the IAB becomes impossible. In addition, when the operator is inserting the IAB, he is not able to, at the same time, continue attempting to deal with the closed artery in order to restore blood circulation. Thus, in various circumstances where an IAB may be helpful, it may be decided that any attempt to insert that device will create more risks than it alleviates.

An attempt to place the IAB in the same femoral artery as that employed for insertion of the PTCA catheter precludes the physician operator from proceeding with attempts at opening the blocked coronary artery, exposing the patient to a higher risk of myocardial infarction and death.

There are also occasions when patients present to the hospital with a myocardial infarction and are hemodynamically unstable with very low blood pressure, cardiogenic shock. A device according to the invention can be placed either in the emergency or catheterization laboratory to provide intra-aortic balloon counterpulsation as a supportive measure while simultaneously allowing for more timely emergency balloon angioplasty as the guiding catheter is already in place ready for the PTCA balloon.

SUMMARY OF THE INVENTION

It is a primary object of the present invention to provide a solution to the above-described problems.

Another object of the invention is to make an IAB immediately available for emergency use during PTCA.

A further object of the invention is to provide apparatus which makes an IAB immediately available at the location needed during a PTCA procedure.

The above and other objects are achieved, according to the present invention, by a medical device for performing percutaneous transluminal coronary angioplasty (PTCA) and intra-aortic balloon (IAB) counterpropulsion, comprising: a guide catheter insertable into a coronary artery, the guide catheter having an outer surface; an IAB mounted on the outer surface of said catheter; and a PTCA catheter insertable into a coronary artery through the guide catheter, the PTCA catheter including an angioplasty balloon.

BRIEF DESCRIPTION OF THE DRAWINGS

The sole Figure is a cross-sectional detail view of the distal end of a preferred embodiment of a medical device according to the present invention.

DESCRIPTION OF THE PREFERRED EMBODIMENTS

A device according to the invention, as illustrated in the Figure, includes a guide catheter 2 having the same shape, structure and dimensions as coronary guide catheters which are currently in use, i.e. catheter 2 is provided with a lumen. Guide catheter 2 is provided, in a region spaced a short distance from its distal end 4, with an annular IAB 6 of conventional construction. Prior to insertion of the medical device into an artery, IAB 6 is wrapped tightly around catheter 2 so as to not interfere with catheter insertion. When needed after insertion, IAB 6 will be inflated by helium gas supplied via a tube or lumen, in the proximal descending aorta in the same manner as that currently employed for IABs. IAB 6 can be connected, via an inflation tube 8, to a conventional console of the type currently in use for inflation with helium gas and deflation, inflation and deflation being timed to the cardiac cycle. Helium gas could be delivered and removed by any conventional technique. When IAB 6 is no longer needed, it can be deflated, and catheter 2 can be removed through the vascular sheath (not shown).

The device according to the invention further includes a PTCA catheter 12 which is dimensioned to be insertable through catheter 2. Catheter 12 has a distal end 14 and is provided, near distal end 14, with an angioplasty balloon 18. Catheter 12 is formed to have a balloon inflation lumen 20 which communicates with the interior of balloon 18 and a further lumen 24 which extends fully to distal end 14. The coronary guide wire extends through lumen 24 into the distal aspect of the instrumented coronary artery.

Catheter 12 is utilized in a conventional manner to perform balloon angioplasty procedures. A considerable benefit offered by the present invention is that catheter 2, when it acts as a guide catheter for PTCA catheter 12, is readily available to function as an IAB, if a medical need for that procedure should arise. Thus, without any significant addition of elements into an artery for angioplasty purposes, the invention makes available an IAB which is in position for immediate use.

A device according to the present invention would be utilized in essentially the manner described earlier herein for conventional PTCA procedures. The differences are that, in place of the hollow plastic catheter mentioned above, guide catheter 2 according to the invention would be inserted to position IAB 6 at an appropriate location in the descending aorta.

A medical device according to the invention would be connected to conventional systems which are located outside of the patient's body and which deliver inflation gases in a controlled manner to IAB 6, via inflation tube 8, and inflation fluids to balloon 18, via inflation lumen 20. Because the systems used for this purpose are conventional and would be connected to tube 8 and lumen 20 in a conventional manner, those systems and their connections are not illustrated herein.

While particular embodiments of the present invention have been shown and described, it will be obvious to those skilled in the art that changes and modifications may be made without departing from this invention in its broader aspects and, therefore, the aim in the appended claims is to cover all such changes and modifications as fall within the true spirit and scope of this invention.

What is claimed is:

1. A procedure for performing percutaneous transluminal coronary angioplasty (PTCA) and intra-aortic balloon (IAB) counterpropulsion with a medical device, the medical device being composed of: a guide catheter insertable into a coronary artery, said guide catheter having an outer surface and a lumen; an IAB mounted on said outer surface of said catheter; and a PTCA catheter insertable into a coronary artery through said guide catheter lumen, said PTCA catheter including an angioplasty balloon, said procedure comprising:

inserting the guide catheter into the coronary artery to position the IAB into a descending aorta of the patient;

inserting the PTCA catheter through the guide catheter lumen to bring the angioplasty balloon to the site of an obstruction in the coronary artery;

inflating the angioplasty balloon to effect radial outward displacement of the obstruction; and responding to hemodynamic instability experienced by the patient by inflating and deflating the IAB in synchronism with the rhythm of the patient's heart.

2. The procedure according to claim 1 wherein said step of inserting the guide catheter into the coronary artery is performed by inserting the guide catheter via a vascular sheath.

* * * * *